US011203726B1

(12) United States Patent
Harvey et al.

(10) Patent No.: US 11,203,726 B1
(45) Date of Patent: Dec. 21, 2021

(54) DIAMONDOID FUELS

(71) Applicant: The United States of America, as represented by the Secretary of the Navy, Arlington, VA (US)

(72) Inventors: Benjamin G. Harvey, Ridgecrest, CA (US); Matthew C. Davis, Ridgecrest, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/835,639

(22) Filed: Mar. 31, 2020

Related U.S. Application Data

(62) Division of application No. 16/178,273, filed on Nov. 1, 2018, now Pat. No. 10,710,941.

(51) Int. Cl.
| | | |
|---|---|---|
| *C10L 1/04* | (2006.01) |
| *C07C 13/615* | (2006.01) |
| *C07C 7/14* | (2006.01) |
| *C10L 1/00* | (2006.01) |
| *C07C 7/11* | (2006.01) |
| *C07C 2/86* | (2006.01) |
| *C07C 7/04* | (2006.01) |
| *C07C 2/56* | (2006.01) |
| *C08L 45/00* | (2006.01) |
| *C07C 22/00* | (2006.01) |

(Continued)

(52) U.S. Cl.
CPC ............... *C10L 1/04* (2013.01); *C07C 2/56* (2013.01); *C07C 2/86* (2013.01); *C07C 7/04* (2013.01); *C07C 7/11* (2013.01); *C07C 7/14* (2013.01); *C07C 13/615* (2013.01); *C07C 22/00* (2013.01); *C08L 45/00* (2013.01); *C10L 1/00* (2013.01); *C06B 43/00* (2013.01); *C10L 10/12* (2013.01)

(58) Field of Classification Search
CPC .. C07C 22/00; C07C 2/56; C07C 2/86; C07C 13/615; C07C 7/14; C07C 7/04; C07C 7/11; C08L 45/00; C10L 10/12; C10L 1/00; C10L 1/04; C10L 1/145; C06B 43/00
See application file for complete search history.

(56) References Cited

U.S. PATENT DOCUMENTS 3,437,701 A    4/1969 Capaldi
3,457,318 A *  7/1969 Borchert ............... C07C 13/615
                                                585/317

(Continued)

OTHER PUBLICATIONS

Synthesis of Adamantane Derivatives REaciton 1-adamantyl chlroide with trimethylsilyl pseudohalideJ Org Chem 46 5445 5447 (Year: 1981).*

(Continued)

*Primary Examiner* — Pamela H Weiss
(74) *Attorney, Agent, or Firm* — Naval Air Warfare Center Weapons Division; Stuart H. Nissim

(57) ABSTRACT

A diamondoid fuel comprising a cage structure including 10, 14, 18, or 22 carbons. The diamondoid fuel also includes one of one to four cyclopropyl groups bonded to the cage structure or two to four functional groups bonded to the cage structure where the functional groups are an alkyl group, an allyl group, a cyclopropyl group, or combinations thereof. Additionally, at least one functional group is an allyl group and at least one functional group is a cyclopropyl group.

4 Claims, 17 Drawing Sheets

(51) Int. Cl.
*C06B 43/00* (2006.01)
*C10L 10/12* (2006.01)

(56) References Cited

U.S. PATENT DOCUMENTS

| | | | |
|---|---|---|---|
| 7,304,190 B2 | 12/2007 | Liu | |
| 2002/0177743 A1* | 11/2002 | Dahl | C07C 49/423 585/16 |
| 2007/0224436 A1* | 9/2007 | Hiraoka | C08J 5/18 428/500 |
| 2007/0255003 A1* | 11/2007 | Watanabe | C07C 17/278 524/553 |
| 2008/0293685 A1* | 11/2008 | Kong | C07C 211/19 514/210.01 |

OTHER PUBLICATIONS

Synthesis of alpha Silylmethyl alphabeta Unsaturated Imines by Rhodium Catalyzed Silylminiation of Primary Alkyl Substituted Terminal Alkyls Fukumoto, Shimizu, Tashiro, Chatani ACS Journal Organic Chem p. 8221-8227 (Year: 2017).*

Electronic and Vibrational Properties of Dioamondoid Oligomers Tyborski, Gillen, Fokin, Koso, Fokina, Hausmann, Rodionov, Schreiner, Thomsen, Maultzsch J Phys Chem 121, 27082-27088 (Year: 2017).*

SciFinder Search Notes (Year: 2020).*

Acid Catalyzed Rearrangement of Tetrahydrotricyclopentadiene for Synthesis of High Density Alkyl Diamondoid Fuel Jiawei Xie Xiangwen Zhang Junjian Xie Jishen Xu Lun Pan Ji Jun Zou Fuel 239 (2019 652-658 (Year: 2019).*

Yoshiya Fukumoto et al., Synthesis of α-Silylmethyl-α,β-Unsaturated Imines by the Rhodium-Catalyzed Silylimination of Primary-Alkyl-Substituted Terminal Alkynes.

Tadashi Sasaki et al., Synthesis of Adamantane Derivatives Reaction of 1-Adamantyl Chloride with Trimethylsilyl Pseudohalide, J. Org. Chem., Jun. 4, 1981, 46, 5445-5447, ACS Pub.

Christoph Tyborski et al., Electronic and Vibrational Properties of Diamondoid Oligomers, J. Phys. Chem. C, Nov. 72017, 121, 27082-27088.

* cited by examiner

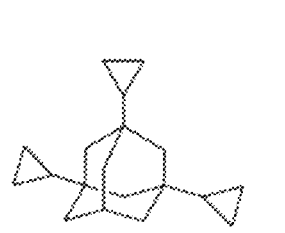 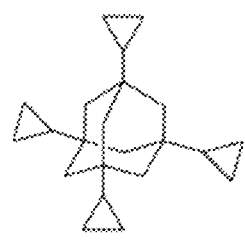  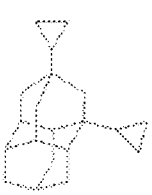 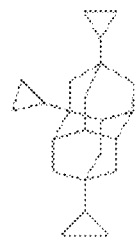
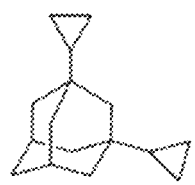 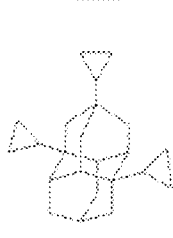 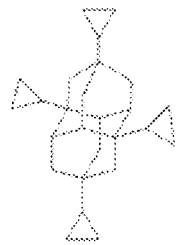
FIG. 3A	FIG. 3B

DIAMONDOID FUELS

CROSS-REFERENCE TO RELATED APPLICATION

This is a divisional patent application of Ser. No. 16/178,273 filed on Nov. 1, 2018. The entire disclosure of patent application Ser. No. 16/178,273 is incorporated by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

Fuel precursors can be chemically produced from petroleum and bio-based sources or obtained from naturally occurring crude oil sources. When producing fuel, the precursors are added to a distillation column with a temperature gradient to separate the various hydrocarbon molecules within the fuel precursor. The hydrocarbon molecules are separated by size and subjected to a specific treatment to produce a fuel for a specific application. For example, jet fuel may contain a mixture of hydrocarbons ranging from 5 to 16 carbon atoms in each molecule.

These hydrocarbons are separated from the column after boiling and specifically treated to produce jet fuel. As a result, distilling a fuel precursor may produce a variety of fuels for different applications in a single distillation.

BRIEF DESCRIPTION OF THE DRAWINGS

Features and advantages of examples of the present disclosure will be apparent by reference to the following detailed description and drawings, in which like reference numerals correspond to similar, though perhaps not identical, components. Reference numerals or features having a previously described function may or may not be described in connection with other drawings in which they appear.

FIGS. 3A-3B are examples of cyclopropyl substituted diamondoid fuels described herein;

DETAILED DESCRIPTION

For fuel, the volumetric net heat of combustion indicates the amount of heat energy that is released for a given volume of fuel that is burned. Fuel with a higher volumetric net heat of combustion releases more heat energy with a given volume of fuel than fuel with a lower volumetric net heat of combustion containing the same volume of fuel. For conventional jet fuel and diesel fuel, the volumetric net heat of combustion is around 125 kBtu/gal and 129 kBtu/gal, respectively.

In the present disclosure, a diamondoid fuel has been produced that has a higher volumetric net heat of combustion compared to conventional jet fuel or diesel fuel (i.e., greater than 129 kBtu/gal). This is due, in part, to the diamondoid fuel having a higher density and, in some instances, a higher ring strain, compared to conventional jet fuel and diesel fuel. As a result, the diamondoid fuels herein can be used as fuel in aircraft or missiles to increase the range of the aircraft or missiles. In addition, in some examples, the diamondoid fuels can be cross-linked to produce polymeric fuels. Therefore, the diamondoid fuels can also form propellants with high volumetric net heats of combustion.

The present disclosure herein includes a method for making a diamondoid fuel. In an example, the method includes reacting a halogenated diamondoid with an allyl halogen in the presence of a Lewis acid catalyst, thereby forming a mixture of diamondoids including halo-alkane functional groups, reacting the mixture of diamondoids with one of i) a reducing metal; or ii) a strong base, thereby forming the diamondoid fuel.

Figure 1:
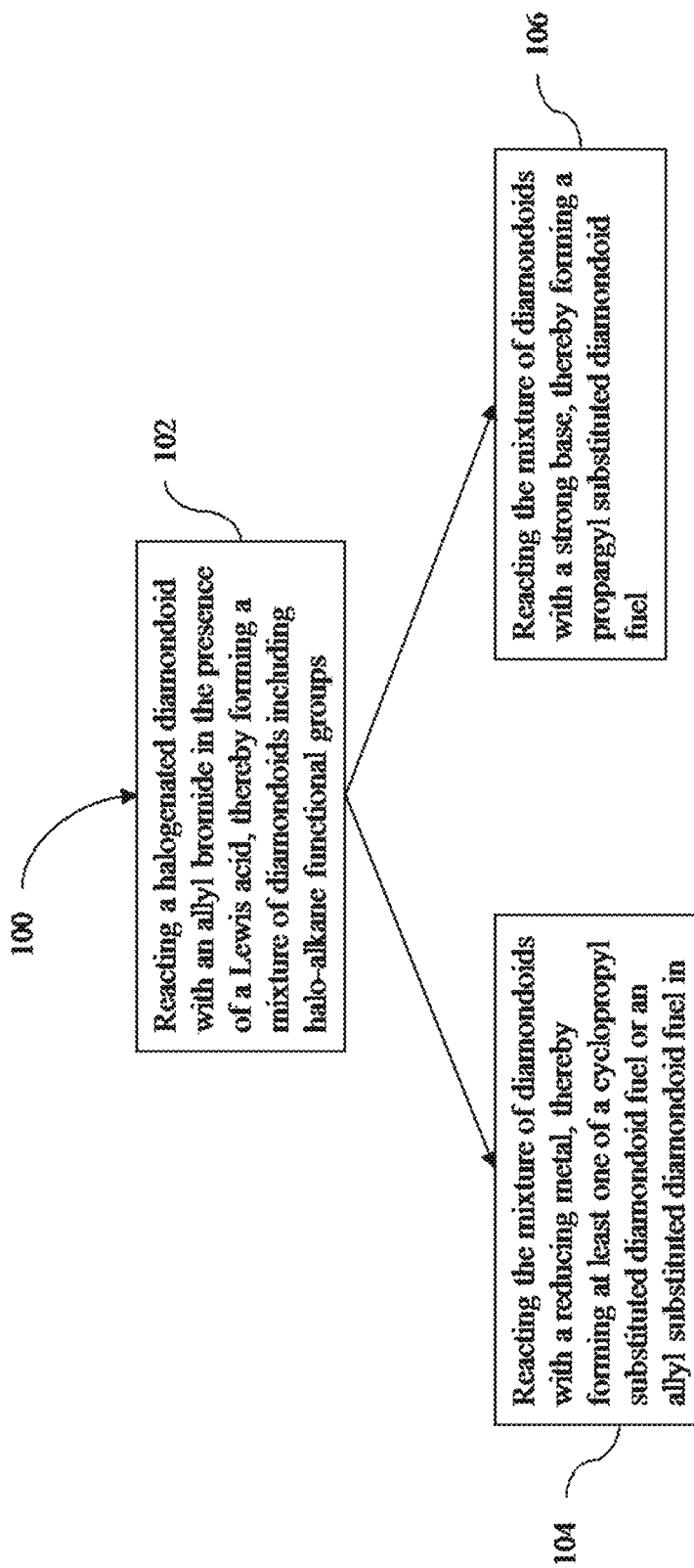
FIG. 1 is a flow diagram illustrating examples of methods for making a diamondoid fuel described herein.

Referring now to FIG. 1, in one example of the method 100 for making a diamondoid fuel, step 102 includes reacting a halogenated diamondoid with an allyl halogen, thereby forming a mixture of diamondoids including halo-alkane functional groups. Halogenated diamondoids and allyl halogens are allowed to react in the presence of a Lewis acid catalyst to form reactive fuel precursors, such as diamondoids including dibromoalkane functional groups. The ability to selectively eliminate the halogens on the halo-alkane functional groups allow for the formation of functional groups including cyclopropanes, allyls, and alkynes. These products can then be used directly as fuels, or undergo polymerization to generate solid or gel-like fuels.

In an example, the reaction between the halogenated diamondoid and the allyl halogen in the presence of a Lewis acid occurs at a temperature ranging from about −80° C. to about 30° C. for a time ranging from about 15 minutes to about 24 hours. The Lewis acid may be any Lewis acid that is capable of accepting an electron pair, such as $AlCl_3$, $AlBr_3$, $BF_3FeCl_3$, and combinations thereof.

A solvent may be used during the reaction to control the type and amount of product that will be obtained in the diamondoid fuel. For example, less polar solvents (e.g., carbon disulfide) form gamma and beta halogenated diamondoids while more polar solvents form alpha and gamma halogenated diamondoids. In another example, solvents with an intermediate polarity form mixtures of grammar, alpha, and beta halogenated diamondoids. Some examples of the solvent include carbon disulfide, a chlorinated solvent (e.g., methylene chloride, tetrachloroethane, 1,2-dichloroethane, 1,1-dichloroethane, or combinations thereof), and combinations thereof.

The allyl halogen functions as an alkylating agent in the synthesis of the diamondoids with halo-alkane functional groups. The allyl halogen may be allyl bromide, allyl iodide, allyl chloride, and combinations thereof.

The halogenated diamondoid provides the multicyclic core of the diamondoid fuels produced herein. The halogenated diamondoid may be a diamondoid with any halogen, such as a bromo-diamondoid, a fluoro-diamondoid, a chloro-diamondoid, an iodo-diamondoid, and combinations thereof. In addition, the halogenated diamondoids may be halogenated adamantanes (10 carbons), halogenated diamantanes (14 carbons), halogenated triamantanes (18 carbons), halogenated tetramantanes (22 carbons), and combinations thereof. Some examples of halogenated diamondoids that may be used in the reaction include any chloroadamantane, bromoadamantane, iodoadamantane, chlorodiamantane, bromodiamantane, or iododiamantane. Some examples of bromo-diamondoids include 1-bromoadamantane, 1,3-dibromoadamantane, 1,3,5-tribromoadamantane, 1,3,5,7-tetrabromoadamantane, adamantanes substituted with bromine at other positions, 1-bromodiamatane, 1,6-dibromodiamantane, 1,4-dibromodiamantane, 4,9-dibromodiamantane, 1,4,9-tribromodiamantane, 1,4,6-tribromodiamantane, 1,4,6,9-tetrabromodiamantane, diamantanes with bromine substituted at other positions, and combinations thereof. Any chloro-analogs, fluoro-analogs, or iodo-analogs of the bromo-diamondoids disclosed herein may also be used. In addition, the halogenated diamondoids may include a range of 1 to 4 halogens.

The mixture of diamondoids including halo-alkane functional groups form reactive fuel precursors of the diamondoid fuels produced by the method 100 herein. The mixture of diamondoids including halo-alkane functional groups may have any of the halogens previously described herein. Additionally, the diamondoid including halo-alkane functional groups may be any of the diamondoids previously described herein. Some examples of the mixture of diamondoids including halo-alkane functional groups are dibromopropane functionalized adamantane or diamantane. In some other examples, the mixture of diamondoids have halo-alkane functional groups with halogens in an alpha position, beta position, gamma position, or combinations thereof, relative to the diamondoid core structure. For example, the halo-alkane functional groups may have halogens on the beta and gamma positions relative to the diamondoid core structure. In another example, the halogens may be on the alpha and gamma positions or the beta and beta positions (of a branched chain fragment) relative to the diamondoid core structure. In other examples, mixtures of halo-alkane functional groups may be generated that have halogens on the beta and gamma, alpha and grammma, or beta and beta positions (of a branched chain fragment) relative to the diamondoid core structure.

In these examples, when the mixture of diamondoids includes halo-alkane functional groups having halogens at the alpha and gamma position or the beta and beta positions (of a branched chain fragment) relative to the diamondoid core structure, the diamondoid fuel produced via a reduction step has cyclopropane groups bonded to the diamondoid. When the mixture of diamondoids includes halo-alkane functional groups having halogens at the beta and gamma positions relative to the diamondoid core structure, the diamondoid fuel produced via a reduction step has allyl groups bonded to the diamondoid. When the mixture of diamondoids includes halo-alkane functional groups having halogens at the beta and gamma positions relative to the diamondoid core structure, the diamondoid fuel produced via a dehydrohalogenation step has propargyl groups bonded to the diamondoid.

Referring back to FIG. 1, in one example of method 100, step 104 includes reacting the mixture of diamondoids with a reducing metal, thereby forming at least one of a cyclopropyl substituted diamondoid fuel or an allyl substituted diamondoid fuel in the mixture. The reducing metal removes the halogens from the diamondoids to form the diamondoid fuel. The diamondoid fuels produced from this step can be used as jet fuel, diesel fuel, or undergo additional reactions to form polymeric fuels depending on the fuel product that is produced.

The reducing metal may be any reducing metal that initiates a Wurtz reaction to remove the halogens from the mixture of diamondoids. The reducing metal may increase the rate of the reaction. Some examples of reducing metals include zinc, aluminum, magnesium, lithium, sodium, potassium, calcium, and combinations thereof. In other examples, the reducing metals have activated surfaces. The reaction between the mixture of diamondoids and the reducing metal produces a cyclopropyl substituted diamondoid fuel, an allyl substituted diamondoid fuel, or a combination thereof depending on the type of halogenated diamondoid used in the reaction as previously discussed herein.

Figure 2B:
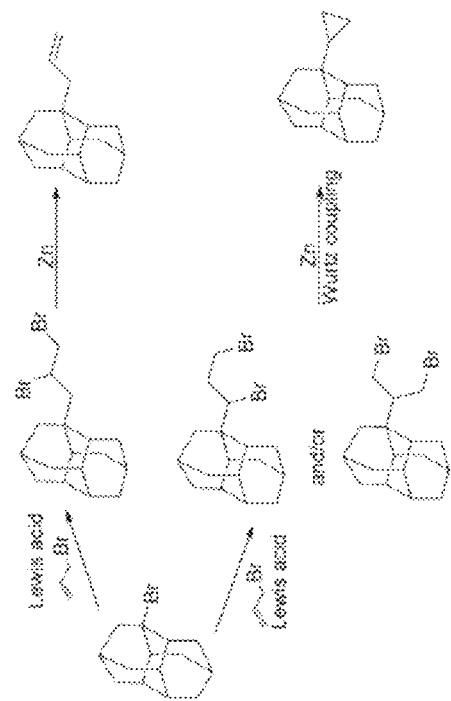
FIGS. 2A-2B are schemes illustrating examples of methods for making a diamondoid fuel described herein.
Figure 2A:
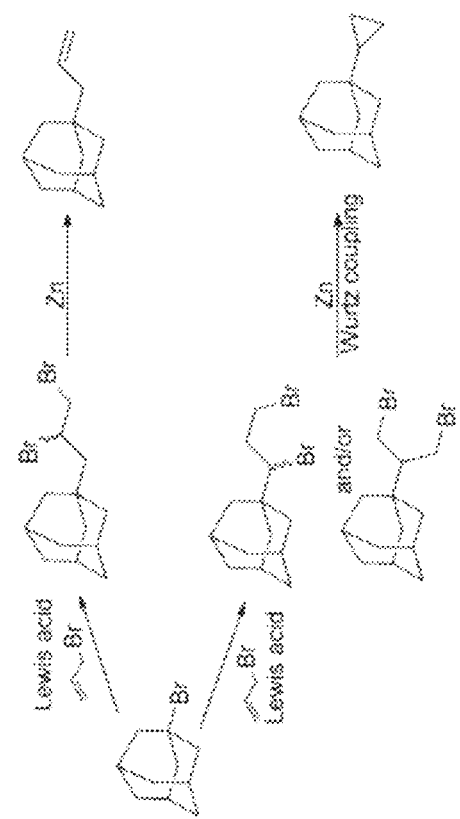

FIGS. 2A and 2B show examples of syntheses using method 100 to produce a cyclopropyl substituted diamondoid fuel or an allyl substituted diamondoid fuel. In FIG. 2A, an adamantane diamondoid fuel is produced. In FIG. 2B, a diamantane diamondoid fuel is produced. In FIGS. 2A and 2B, an allyl bromide is reacted with a halogenated diamondoid in the presence of a Lewis acid to produce a mixture of diamondoids including dibromoalkane functional groups. In FIGS. 2A and 2B, the mixture of diamondoids undergoes a Wurtz coupling using a zinc reducing metal to produce a cyclopropyl substituted adamantane fuel or a cyclopropyl substituted diamantane fuel. In FIGS. 2A and 2B, when the mixture of diamondoids undergoes a reductive elimination, an allyl substituted adamantane fuel or an allyl substituted diamantane fuel is generated.

In examples of the method 100 herein, the diamondoid fuel produced may include a cage structure. The cage structure may be an adamantane (10 carbons), a diamantane (14 carbons), a triamantane (18 carbons), a tetramantane (22 carbons), and combinations thereof. It is to be understood that the triamantanes and tetramantanes include any triamantane and tetramantane isomers. In one example, the cage structure may have one to four cyclopropyl groups, allyl groups, or alkyl groups with 1 to 20 carbons bonded to the cage structure. In another example, the cage structure has two to four functional groups with at least one allyl group and at least one cyclopropyl group bonded to the cage structure. In yet another example, the cage structure may have one to four propargyl groups bonded to the cage structure.

Some specific examples of the diamondoid fuel include an adamantane cage structure or a diamantane cage structure, which are shown below in the chemical structures (I) and (II), respectively:

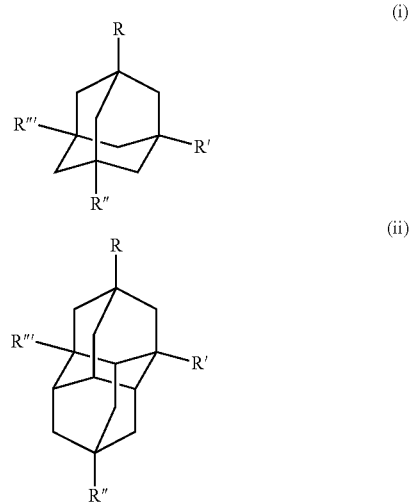

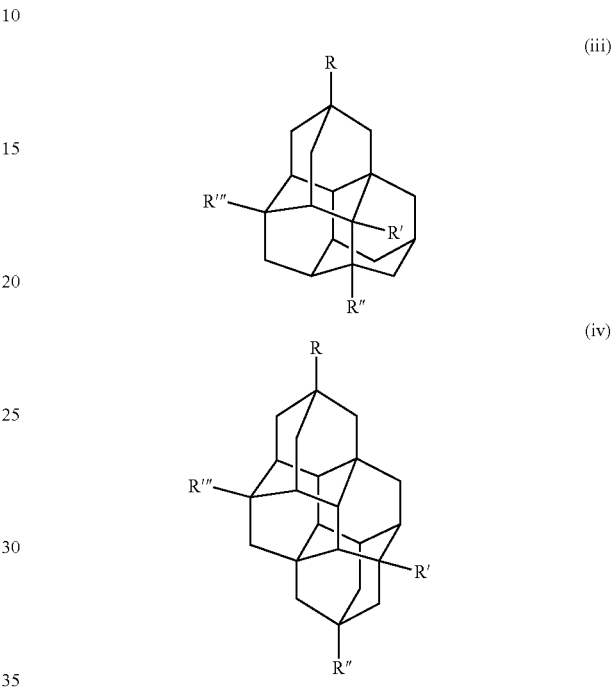

In this example, R, R', R", and R'" in the chemical structure (i) and the chemical structure (ii) are each independently a hydrogen, an allyl group, a cyclopropyl group, an alkyl group with 1 to 20 carbons, or combinations thereof. At least one of R, R', R", or R'" is an allyl group and at least one of R, R', R", or R'" is a cyclopropyl group. In another example, R, R', R", and R'" in the chemical structure (i) and the chemical structure (ii) are each independently a hydrogen, a cyclopropyl group, or combinations thereof, where at least one of R, R', R", or R'" is a cyclopropyl group.

Figure 4:
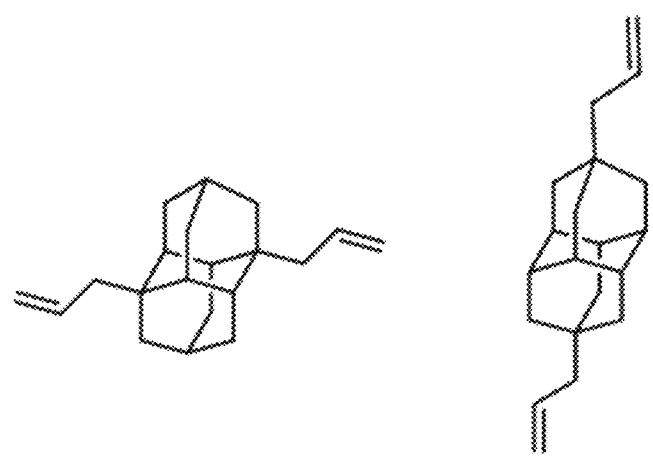
FIG. 4 is examples of allyl substituted diamondoid fuels described herein.

The chemical structures of different examples of adamantane and diamantane diamondoid fuels are shown in FIG. 3A, FIG. 3B, and FIG. 4. FIG. 3A shows some specific examples of chemical structures for cyclopropyl substituted adamantane fuels. FIG. 3B shows some specific examples of chemical structures for cyclopropyl substituted diamantane fuels.

FIG. 4 shows some specific examples of chemical structures for allyl substituted diamantane fuels.

Some specific examples of adamantane and diamantane diamondoid fuels produced herein include 1-cyclopropyladamantane, 1,3-dicyclopropyladamantane, 1,3,5-tricyclopropyladamantane, 1,3,5,7-tetracyclopropyladamantane, 1-allyladamantane, 1,3-diallyadamantane, 1,3,5-triallyladamantane, 1,3,5,7-tetraallyladamantane, 1,6-dicyclopropyldiamantane, 1,4-dicyclopropyldiamantane, 4,9-dicyclopropyldiamantane, 1,4,9-tricyclopropyldiamantane, 1,4,6-tricyclopropyldiamantane, 1,4,6,9-tetracyclopropyldiamantane, 1,6-diallyldiamantane, 1,4-diallyldiamantane, 4,9-diallyldiamantane, 2,11-diallyldiamantane, 1,4,9-triallyldiamantane, 1,4,6-triallyldiamantane, 1,4,6,9-tetraallyldiamantane, and combinations thereof. It is to be understood that the diamondoid fuel examples listed above can also include alkyl groups and cyclopropyl groups, alkyl and allyl groups (instead of cyclopropyl groups), alkyl, cyclopropyl, and allyl groups, or alkyl and propargyl groups (instead of cyclopropyl groups).

Other examples of the diamondoid fuel include a triamantane cage structure or a tetramantane cage structure, which are shown below in chemical structures (iii) and (iv), respectively:

In this example, R, R', R", and R'" in the chemical structure (iii) and the chemical structure (iv) are each independently a hydrogen, an allyl group, a cyclopropyl group, an alkyl group with 1 to 20 carbons, or combinations thereof. At least one of R, R', R", or R'" is an allyl group and at least one of R, R', R", or R'" is a cyclopropyl group. In another example, R, R', R", and R'" in the chemical structure (iii) and the chemical structure (iv) are each independently a hydrogen, a cyclopropyl group, or combinations thereof, where at least one of R, R', R", or R'" is a cyclopropyl group. It is to be understood that chemical structures (iii) and (iv) include any isomers of the triamantane and tetramantane structures described herein.

Some specific examples of triamantane and tetramantane diamondoid fuels produced herein include 3,6-diallyl-13-cyclopropyltriamantane, 3,6,13-triallyl-19-cyclopropyltriamantane, 3-allyltriamantane, 3,13-diallyltriamantane, 3,6,13-triallyltriamantane, 3,11-diallyl-19-cyclopropyltetramantane, 3,11,19-triallyl-6-cyclopropyltetramantane, 3-allytetramantane, 3,11-diallyltetramantane, 3,11,19-triallyltetramantane, and combinations thereof.

Referring back to method 100, in one example, step 104 can further include separating the cyclopropyl substituted diamondoid fuel from the mixture of diamondoids when the mixture includes the cyclopropyl substituted diamondoid fuel and the allyl substituted diamondoid fuel. After separation, the cyclopropyl substituted diamondoid fuel may be used as jet, missile, or diesel fuel. Some examples of methods for separating the cyclopropyl substituted diamondoid fuel include fractional distillation, crystallization, or selective removal of the allyl substituted diamondoid fuel using a reversible binding absorbent (e.g., chromatography with silica gel or alumina or silica gel treated with silver salts).

After removal of the cyclopropyl substituted diamondoid fuel, the allyl substituted diamondoid fuel may be polymerized, cross-linked, or polymerized and cross-linked to form a polymeric diamondoid fuel. The cross-linking or polymerization may be performed using any known polymerization technique. For example, polymerization may be accomplished using anionic polymerization, free radical polymerization, Ziegler-Natta polymerization, or thermal polymerization. The resulting polymeric diamondoid fuel may be used in propellant formulations or hydrogenated and used as jet or diesel fuel.

Referring back to method 100, in yet another example, step 104 may include cross-linking the cyclopropyl substituted diamondoid fuel and the allyl substituted diamondoid fuel using a thiol-ene reaction or an olefin metathesis reaction to form a polymeric diamondoid fuel. In an example, thiol-ene reactions would entail the reaction of a dithiol or polythiol with monomers, oligomers, or polymers containing alkenes. The thiol-ene reaction may be accelerated by UV irradiation and heating or using catalysts, such as peroxides, photosensitizers, and hindered amines. In another example, olefin metathesis reactions can be performed using a catalyst, such as ruthenium, molybdenum, or tungsten. The polymeric diamondoid fuel may include both the cyclopropyl groups and the allyl groups.

Referring now to method 100, step 106 includes reacting the mixture of diamondoids with a strong base, thereby forming a propargyl substituted diamondoid fuel. The strong base causes dehydrohalogenation of the mixture of diamondoids. This step 106 may be performed at a temperature ranging from about 20° C. to about 150° C. The propargyl substituted diamondoid fuel can be cross-linked in a subsequent step and used in a propellant formulation as a binder or additive.

Figure 5A:
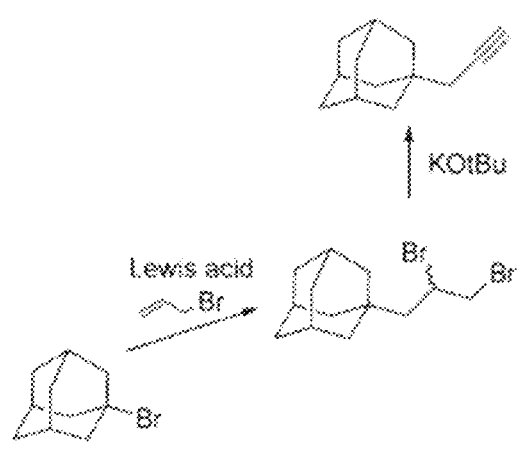
FIGS. 5A-5B are schemes illustrating other examples of methods for making a propargyl diamondoid fuel described herein.
Figure 5B:
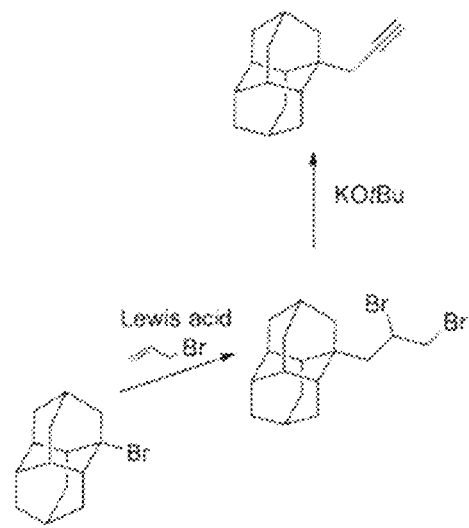

The strong base may be any strong base that causes dehydrohalogenation. Some examples of a strong base that may be used are potassium tert-butoxide, alkali alkoxides, alkaline alkoxides, and combinations thereof. FIG. 5A-5B show examples of syntheses where a strong base is reacted with diamondoids including dibromoalkane functional groups. FIG. 5A includes an adamantane diamondoid with dibromoalkane functional groups. FIG. 5B includes a diamantane diamondoid with dibromoalkane functional groups. In both FIGS. 5A and 5B, a propargyl substituted diamondoid fuel is produced from the reaction with a strong base.

Figures 6A, 6B:
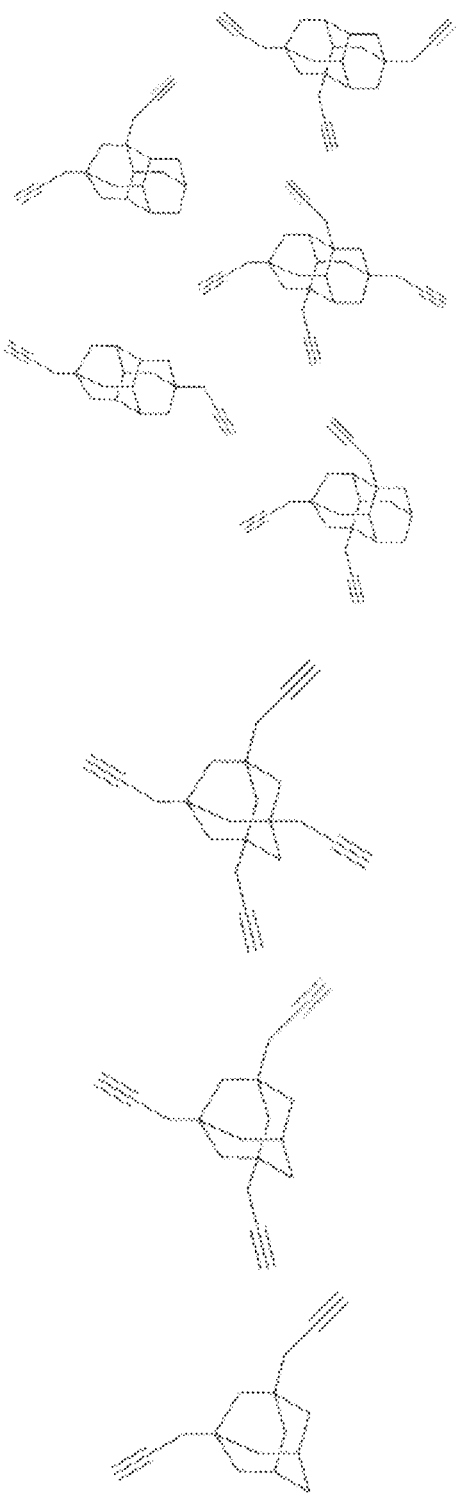
FIGS. 6A-6B are examples of propargyl substituted diamondoid fuels described herein.

Some specific examples of propargyl substituted diamondoid fuels include, 1-propargyladamantane, 1,3-dipropargyladamantane, 1,3,5-tripropargyladamantane, 1,3,5,7-tetrapropargyladamantane, 2,11-dipropargyldiamantane, and 4.9-dipropargyldiamantane, and combinations thereof. Propargyl substituted diamondoids may also include a propargyl group and another alkyl group if the halogenated diamondoid has other alkyl groups prior to the reaction with the strong base. FIGS. 6A and 6B show examples of chemical structures for propargyl substituted diamondoid fuels. FIG. 6A shows examples of propargyl substituted adamantane fuels. FIG. 6B shows examples of propargyl substituted diamantane fuels. The propargyl substituted diamondoid fuels may also be formed with triamantanes or tetramantanes previously described herein.

Referring back to FIG. 1, step 106 can further include cross-linking the propargyl substituted diamondoid fuel, thereby forming a polymeric diamondoid fuel. In some examples, a catalyst is used to cross-link the substituted diamondoid fuel. Some examples of the catalyst include transition metal catalysts, where the transition metals in the catalyst include Co, Rh, or Ru. The polymeric diamondoid fuel may be used in a propellant. The propargyl substituted diamondoid fuel may be cross-linked using alkyne cyclotrimerization, by the application of heat (e.g., from about 25° C. to about 350° C.), alkyne metathesis, or an alkene metathesis.

To further illustrate the present disclosure, examples are given herein. It is to be understood that these examples are provided for illustrative purposes and are not to be construed as limiting the scope of the present disclosure.

EXAMPLES

Example 1: Preparing a 1-(allyl)adamantane Diamondoid Fuel

Figure 7:
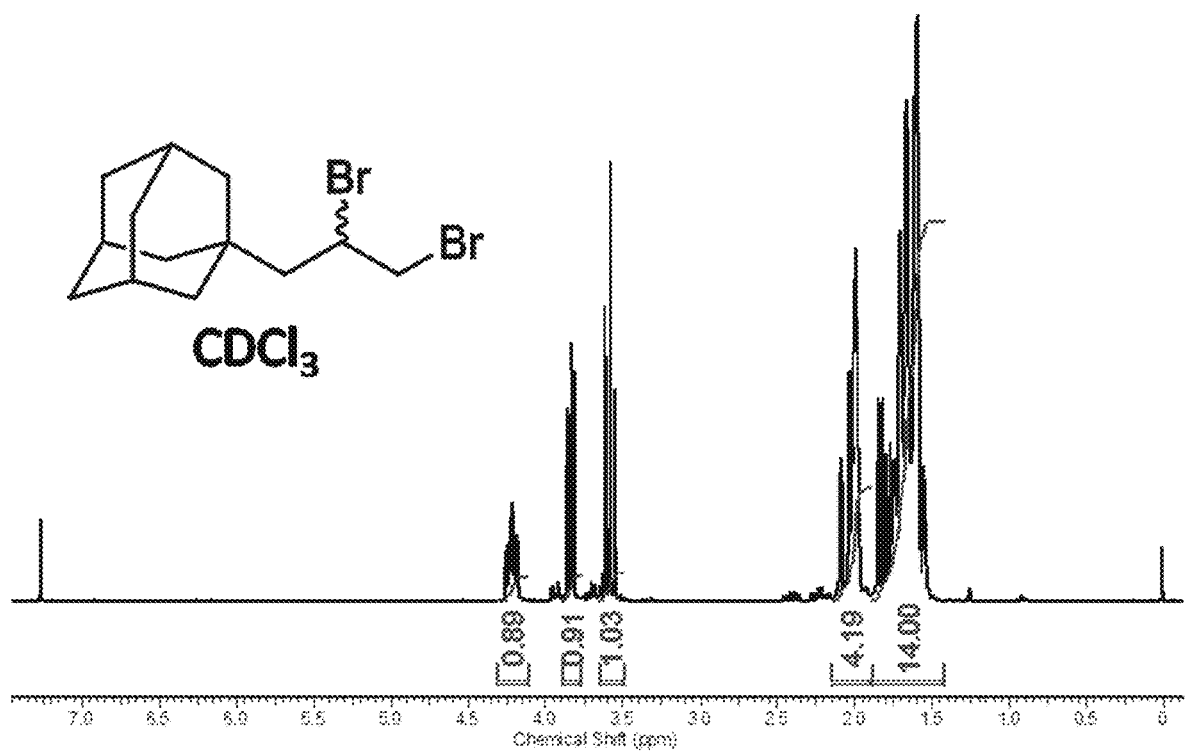
FIG. 7 is an $^1$H NMR spectrum of a diamondoid including one dibromoalkane functional group at the beta and gamma positions.

In this example, 1-bromoadamantane (10.8 g, 50 mmol) and allyl bromide (6.05 g, 50 mmol) were dissolved in carbon disulfide (40 mL) and the solution was cooled to −78° C. In a single portion, anhydrous $AlCl_3$ (0.5 g, 3 mmol) was added to the reaction mixture. The reaction was then allowed to warm to −55° C. and stirred for 1 hour. While still cold, water was added to quench the reaction. The product is shown in the $^1H$ NMR spectrum in FIG. 7, which is consistent with the structure for 1-(2,3-dibromopropanyl)adamantane.

Figure 8:
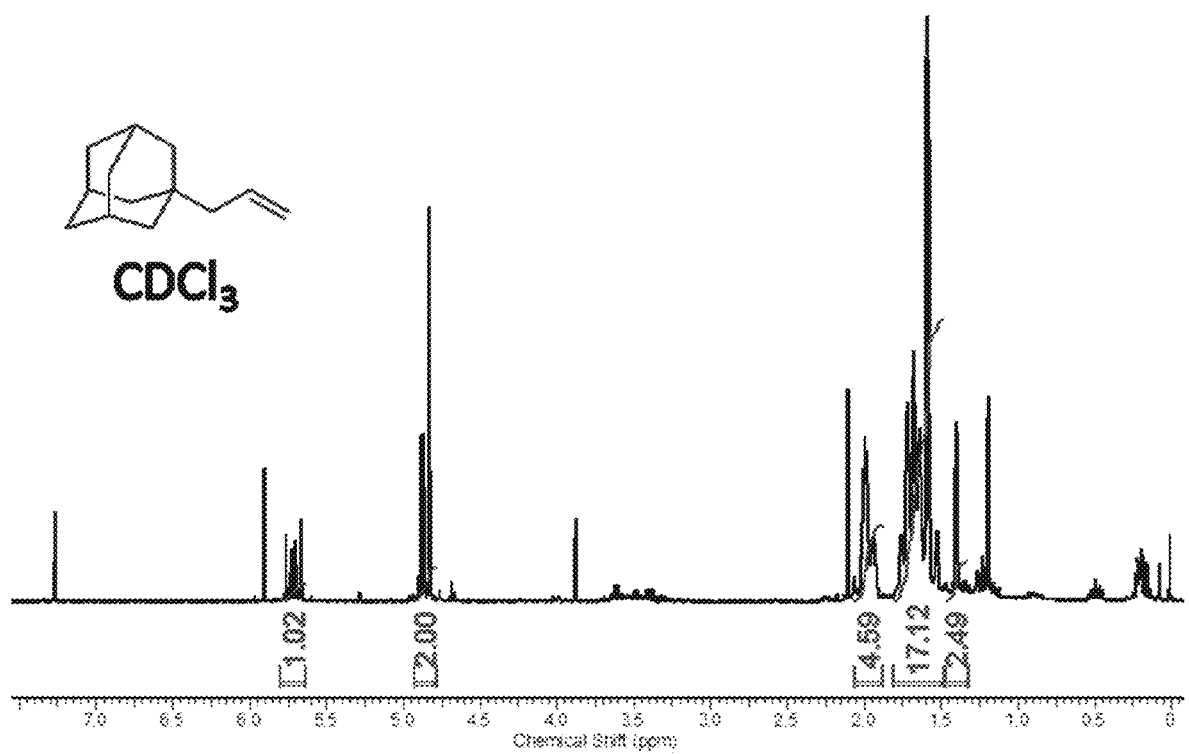
FIG. 8 is an $^1$H NMR spectrum of an example of an allyl substituted diamondoid fuel.

The 1-(2,3-dibromopropanyl)adamantane product was then used to prepare a mixture of diamondoids. 1-(2,3-dibromopropanyl)adamantane (3.36 g, 10 mmol), zinc dust (1.3 g, 20 mmol) and anhydrous ethanol (25 mL) were combined and the mixture was refluxed for 5 hours. The mixture was cooled to room temperature, filtered, the solvent was rotary evaporated, and a product residue was obtained. The residue was further distilled at reduced pressure (0.1 torr) to obtain the purified fuel product. The $^1H$ NMR spectrum of the fuel product is shown in FIG. 8, and confirms the presence of 1-(allyl)adamantane due to the distinctive coupling pattern of the alkene resonances observed between 4 ppm to 6 ppm.

Example 2: Preparing a 1,3-bis(allyl)adamantane Diamondoid Fuel

Figure 9:
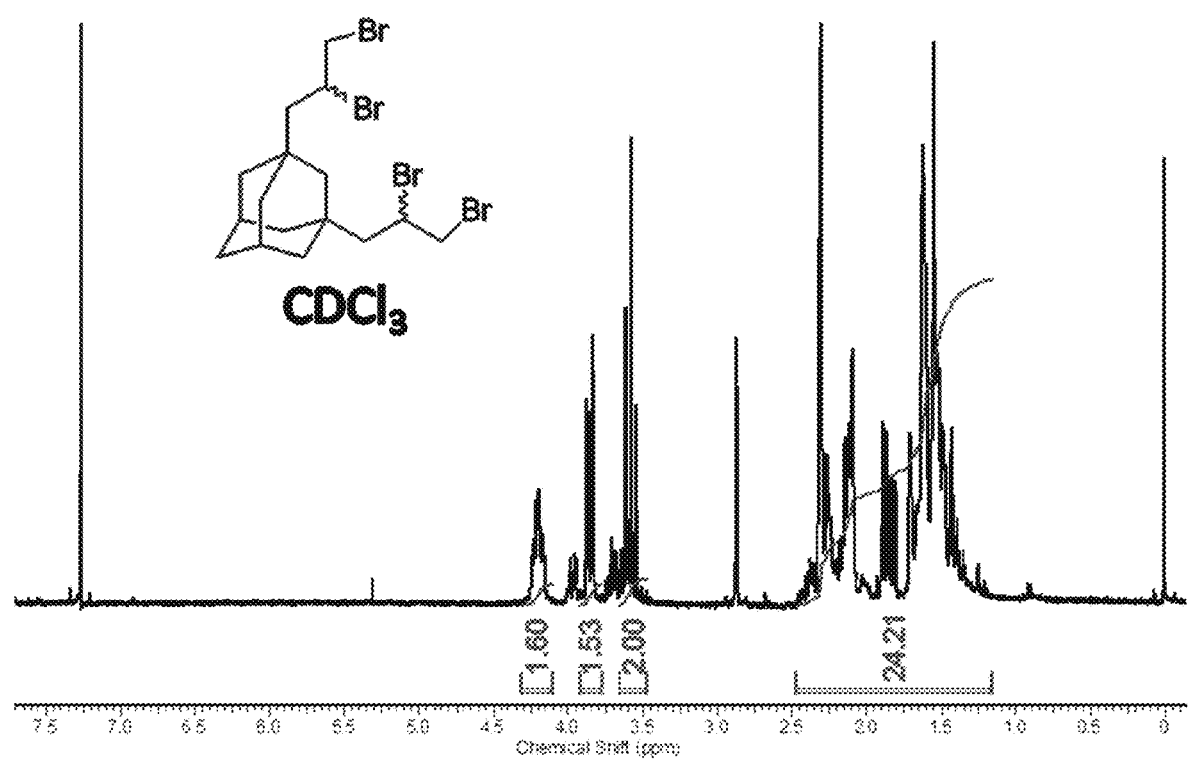
FIG. 9 is an $^1$H NMR spectrum of a diamondoid including two dibromoalkane functional groups at the beta and gamma positions.

In this example, 1,3-dibromoadamantane (3.3 g, 11 mmol) and allyl bromide (3 g, 24 mmol, 2.2 equiv) were dissolved in carbon disulfide (40 mL) and the solution was cooled to −78° C. anhydrous $AlCl_3$ (250 mg) and methylene chloride (25 mL) were added to the reaction mixture. The reaction was then allowed to warm to −55° C. and stirred for one hour. While still cold, water was added to quench the reaction. After a standard workup, the product, 1,3-bis(2,3-dibromopropanyl)adamantane, was obtained as a viscous oil. The $^1H$ NMR spectrum of the product is shown in FIG. 9, and is consistent with the expected orientation of the bromine substituents.

Figure 10:
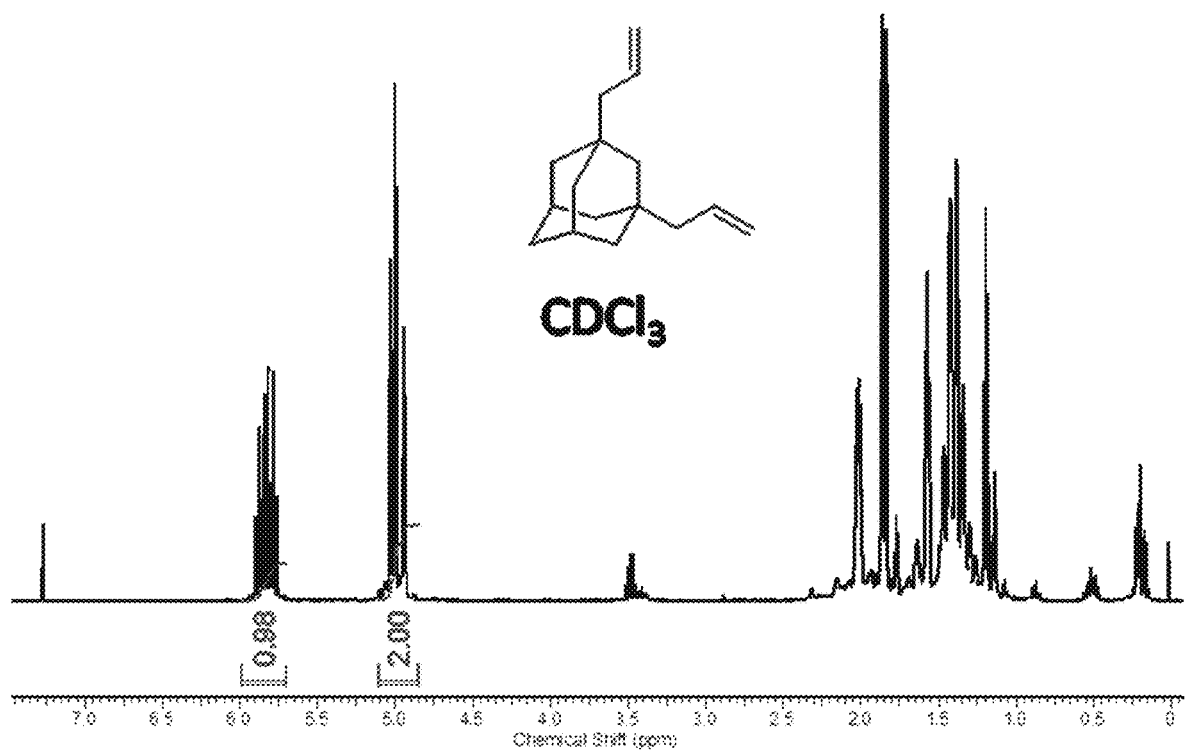
FIG. 10 is an $^1$H NMR spectrum of another example of an allyl substituted diamondoid fuel.

The 1,3-bis(2,3-dibromopropanyl)adamantane product was then used to prepare a mixture of diamondoids. 1,3-bis(2,3-dibromopropanyl)adamantane (3.36 g, 6 mmol), zinc dust (1.3 g, 20 mmol) and anhydrous ethanol (25 mL) were combined, the mixture was refluxed for 5 hours. After a standard workup and removal of low boiling volatile compounds, a product residue was obtained. The residue was further distilled at reduced pressure (0.1 torr) to obtain the purified fuel product. The $^1H$ NMR spectrum of the fuel product is shown in FIG. 10, and confirms the presence of the product, 1,3-bis(allyl)adamantane.

Example 3: Preparing a 1-(cyclopropyl)adamantane Diamondoid Fuel

Figure 11:
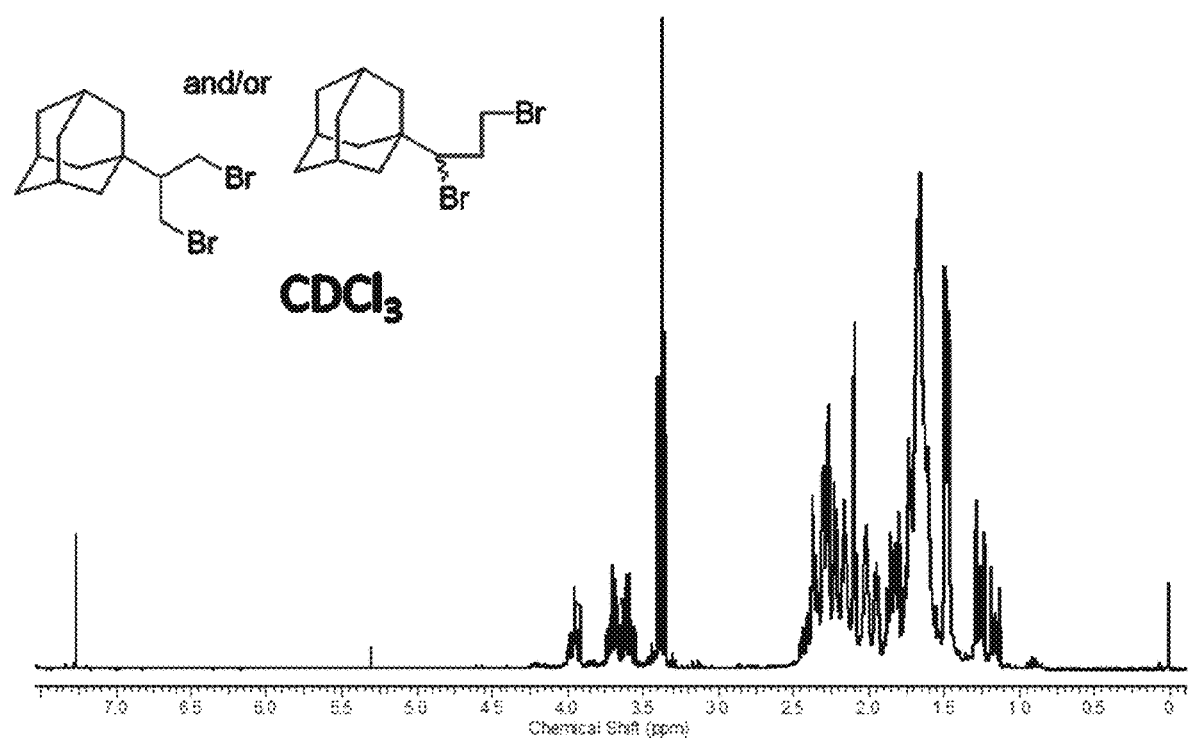
FIG. 11 is an $^1$H NMR spectrum of a diamondoid including one dibromoalkane functional group at the beta and beta (of a branched chain fragment) positions or alpha and gamma positions.

In this example, 1-bromoadamantane (2.7 g, 12 mmol) and allyl bromide (1.51 g, 12 mmol, 1 equiv) were dissolved in carbon disulfide (40 mL) and the solution was cooled to −55° C. In a single portion, anhydrous $AlCl_3$ (125 mg) and methylene chloride (20 mL) were added to the reaction mixture. The reaction was then allowed to warm to −30° C. and stirred for 1 hour. While still cold, water was added to quench the reaction. The $^1$H NMR spectrum of the product is shown in FIG. 11. The peaks observed from 4 ppm to 3.5 ppm are associated with a mixture of beta/beta and alpha/gamma dibromopropanyl groups bonded to the adamantane ring.

Figure 12:
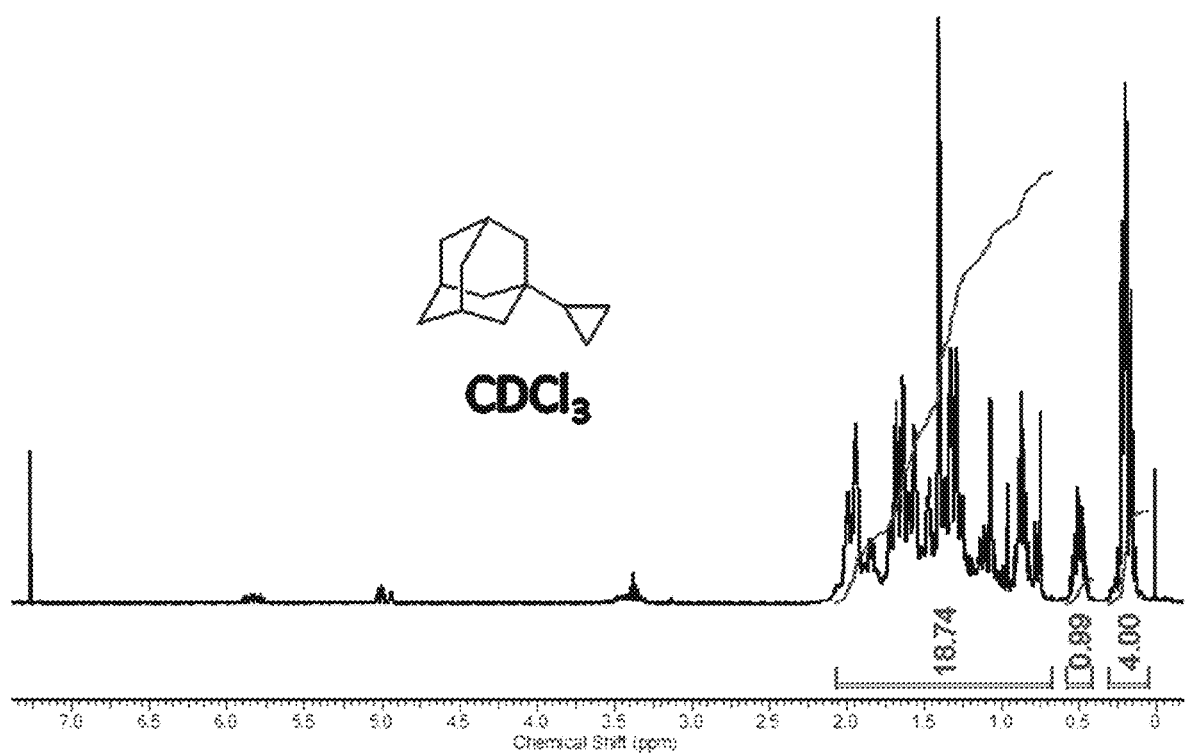
FIG. 12 is an $^1$H NMR spectrum of an example of a cyclopropyl substituted diamondoid fuel.

The product was then used to prepare a mixture of 1-cyclopropyladamantane and 1-allyladamantane. The mixture of dibromopropanyl substituted adamantanes (3.36 g, 6.3 mmol), zinc dust (1.3 g, 20 mmol) and anhydrous ethanol (25 mL) were combined, and the mixture was refluxed for 5 hours. After a standard workup and removal of low boiling volatiles, a product residue was obtained. The residue was further distilled at reduced pressure (0.1 torr) to obtain the purified fuel product. The $^1$H NMR spectrum of the fuel product is shown in FIG. 12, which indicates the presence of 1-cyclopropyladamantane. The presence of a cyclopropane ring was confirmed by the observance of characteristic coupled multiplets at 0.2 ppm (4H) and 0.5 ppm (1H).

Example 4: Preparing a 1,3-dicyclopropyladamantane Diamondoid Fuel

Figure 13:
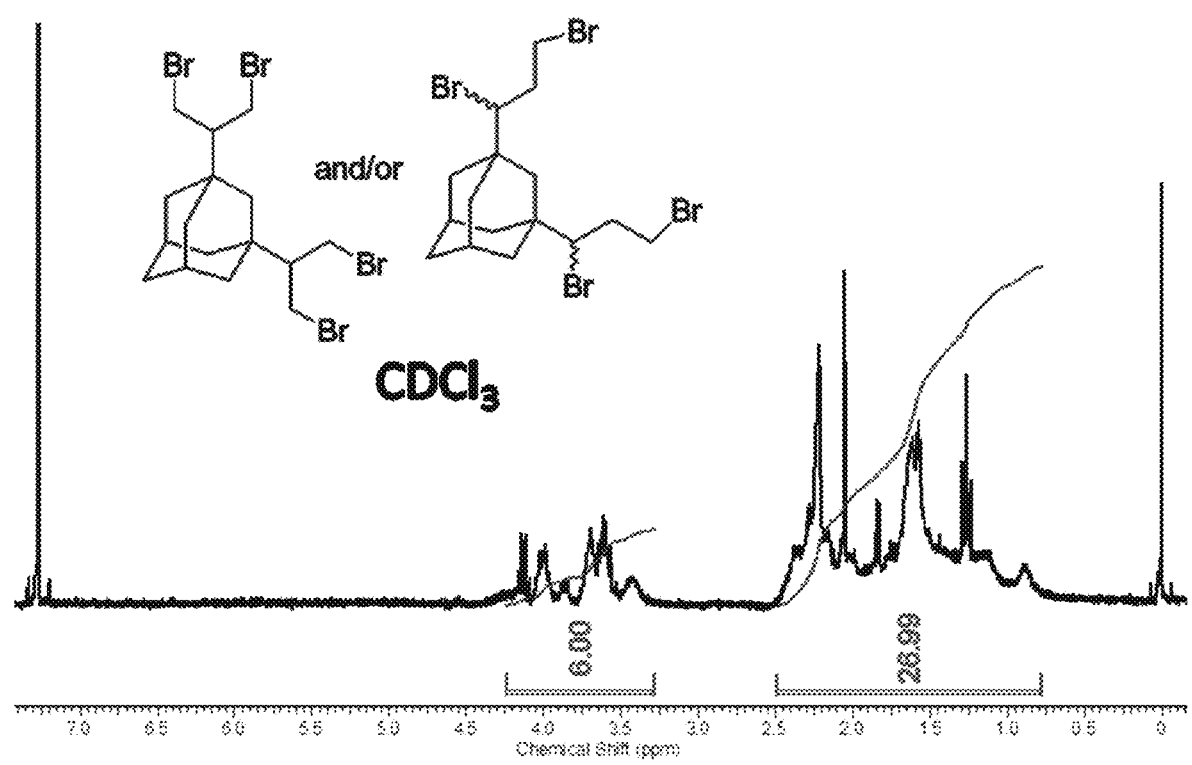
FIG. 13 is an $^1$H NMR spectrum of a diamondoid including two dibromoalkane functional groups at the beta and beta (of a branched chain fragment) positions, alpha and gamma positions, or both the beta and beta (of a branched chain fragment) positions and the alpha and gamma positions.

In this example, 1,3-dibromoadamantane (2 g, 6 mmol) and allyl bromide (2.8 g, 23 mmol) were dissolved in carbon disulfide (40 mL) and the solution was cooled to −55° C. In a single portion, anhydrous $AlCl_3$ (264 mg) and methylene chloride (20 mL) were added to the reaction mixture. The reaction was then allowed to warm to −30° C. and stirred for 1 hour. While still cold, water was added to quench the reaction. The $^1$H NMR spectrum of the product is shown in FIG. 13. The peaks observed from 4.5 ppm to 3.4 ppm indicate that the dibromopropanyl groups were in the beta/beta and/or alpha/gamma positions.

Figure 14:
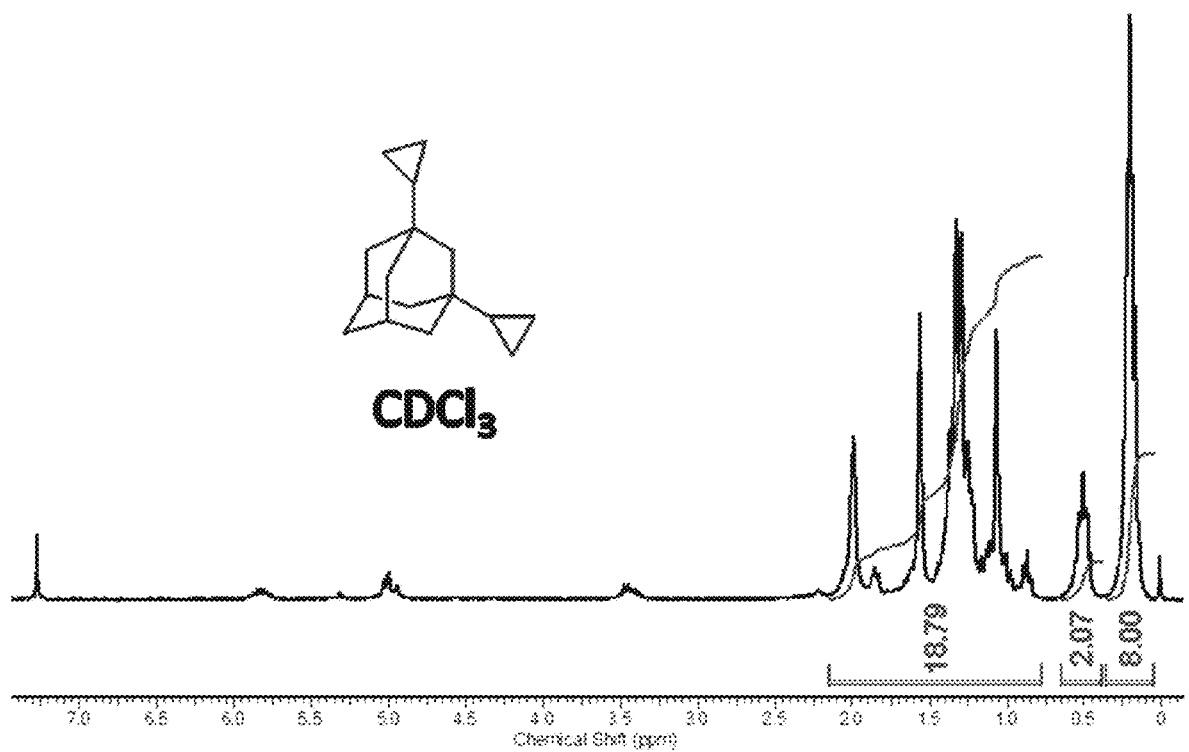
FIG. 14 is an $^1$H NMR spectrum of another example of a cyclopropyl substituted diamondoid fuel.
Figure 15:
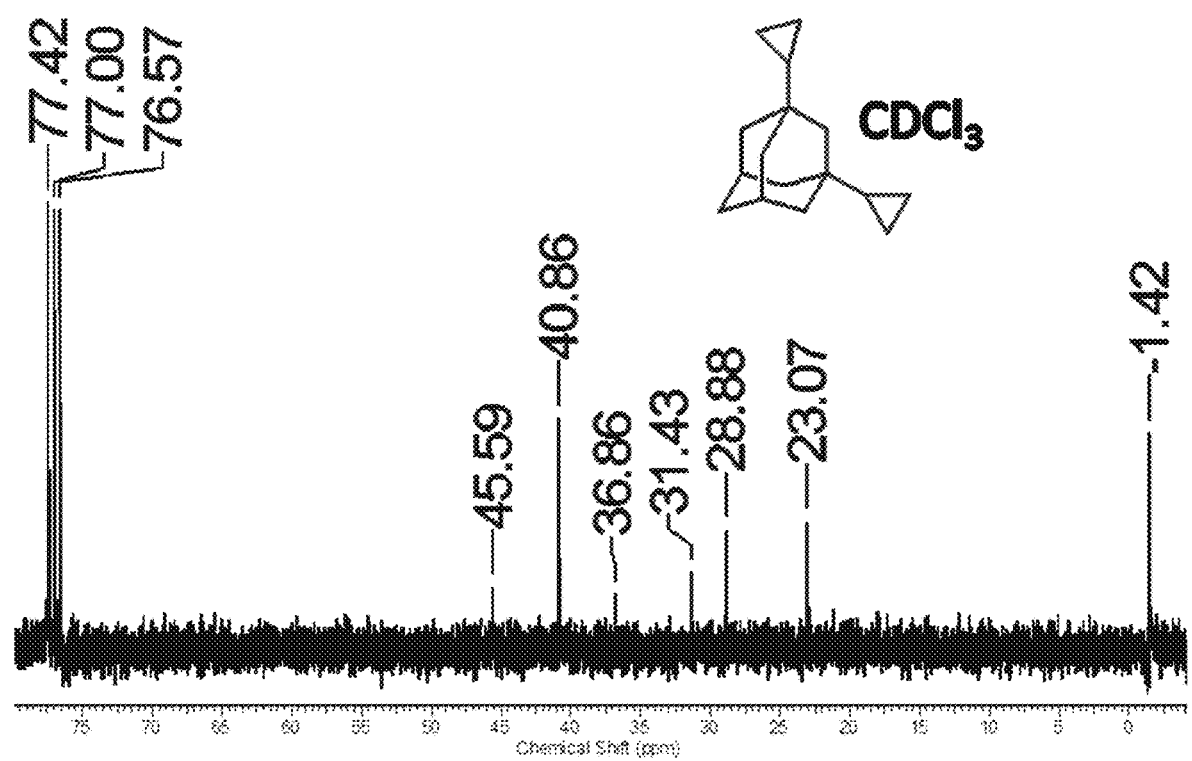
FIG. 15 is a $^{13}$C NMR spectrum of an example of a cyclopropyl substituted diamondoid fuel.

The product was then used to prepare a mixture of the product diamondoids. The diamondoids including two dibromoalkane functional group (3.36 g, 6 mmol), zinc dust (1.3 g, 20 mmol) and anhydrous ethanol (25 mL) were combined and the mixture was refluxed for 3 hours. After a standard workup and removal of low boiling compounds, a liquid product residue was obtained. The residue was further distilled at reduced pressure (0.1 torr) to obtain the purified fuel product as a colorless oil. $^1$H NMR spectrum of the fuel product is shown in FIG. 14, and indicates the presence of two cyclopropane rings, observed as multiplets at 0.2 ppm and 0.5 ppm. In addition, the $^{13}$C NMR spectrum in FIG. 15 shows a characteristic signal at −1.1 ppm for the cyclopropane group, providing further support for the presence of 1,3-dicyclopropyladamantane.

Example 5: Preparing a 1-propargyladamantane Diamondoid Fuel

In this example, a round-bottomed flask (50 mL) equipped with magnetic stirring bar and reflux condenser was filled with 1-(2,3-dibromopropanyl)adamantane (1.68 g, 5 mmol) and dissolved in carbon disulfide (40 mL) and the solution was cooled to −78° C. In a single portion, anhydrous tetrahydrofuran (20 mL) was added to the reaction mixture. The mixture was stirred in an ice bath before potassium tert-butoxide (1.68 g, 15 mmol, 3 equivalents) was added to the mixture in one portion. The cooling bath was then removed and the mixture was stirred at room temperature for 30 minutes. Then the mixture was refluxed for 20 min. The mixture was cooled to room temperature and partitioned between diethyl ether and water. The organic layer was washed again with water followed by brine. The organic phase was separated and dried over anhydrous $MgSO_4$ and then rotary evaporated to a colorless oil product that required no further purification.

Figure 16:
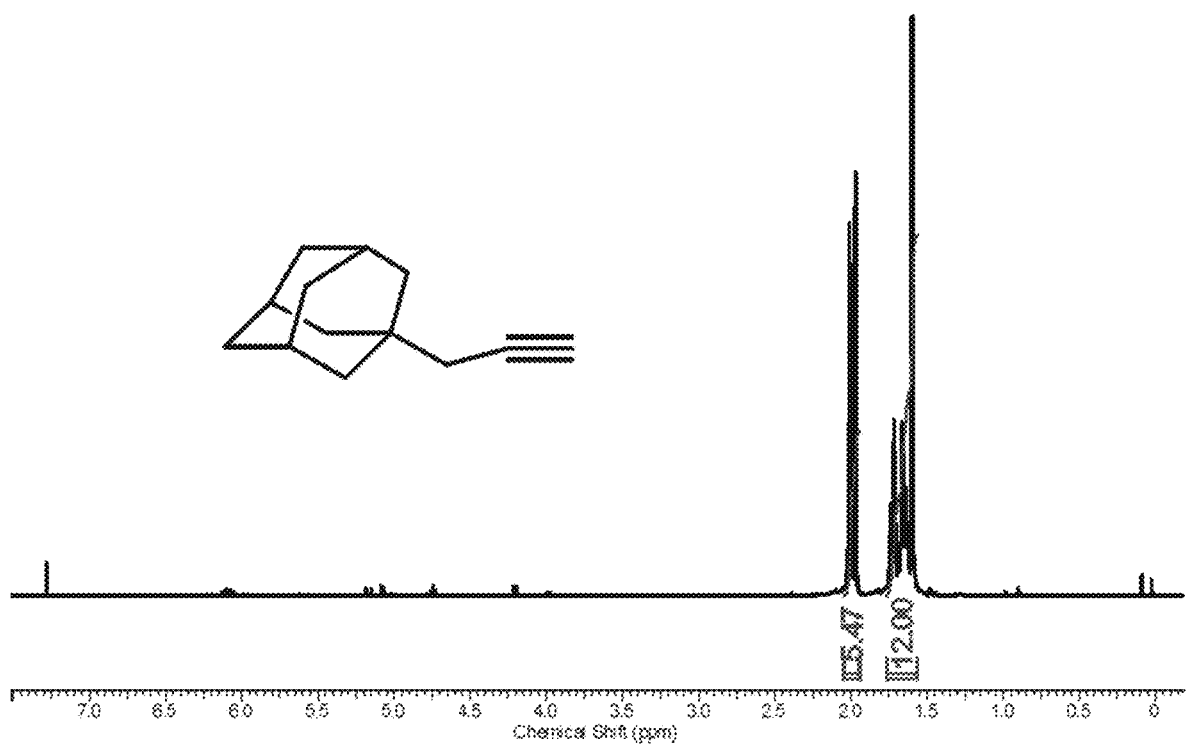
FIG. 16 is an $^1$H NMR spectrum of another example of a propargyl substituted diamondoid fuel.
Figure 17:
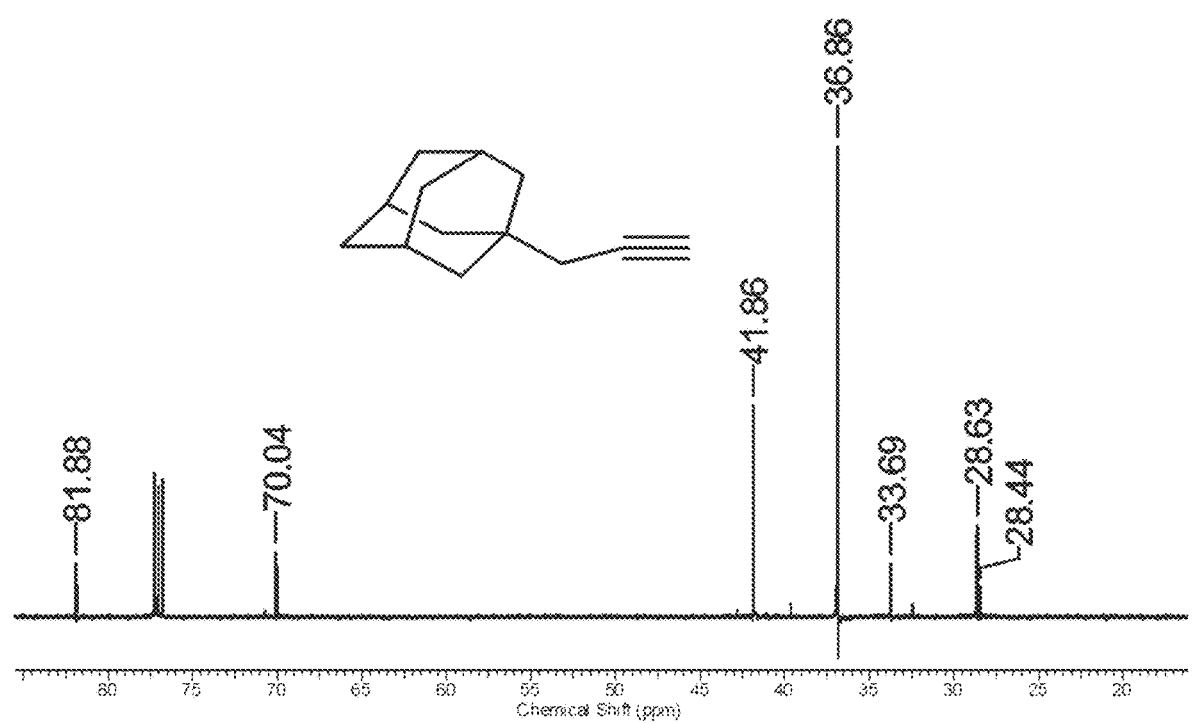
FIG. 17 is a $^{13}$C NMR spectrum of an example of a propargyl substituted diamondoid fuel.

FIG. 16 shows the $^1$H NMR spectrum of the 1-propargyladamantane product that was obtained. FIG. 17 shows the $^{13}$C NMR spectrum of the 1-propargyladamantane product that was obtained. The nuclear magnetic resonance spectra of the product show that it was 1-propargyladamantane based on the alkyne proton that is part of the multiplet at ~2.0 ppm and the alkyne carbon signals are at 70 and 81 ppm which are characteristic of 1-propargyladamantane.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Unless otherwise stated, any feature described herein can be combined with any aspect or any other feature described herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about −80° C. to about 30° C. should be interpreted to include not only the explicitly recited limits of from about −50° C. to about 0° C., but also to include individual values, such as −25° C., 15° C., 25° C., etc., and sub-ranges, such as from about −40° C. to about 0° C., etc.

In describing and claiming the examples disclosed herein, the singular forms "a", "an", and "the" include plural referents unless the context clearly dictates otherwise.

What is claimed is:
1. A polymeric diamondoid fuel, consisting of one or more distinct repeating units where each of said repeating units is a monomer having a stricture selected from one of i, ii, or iii:

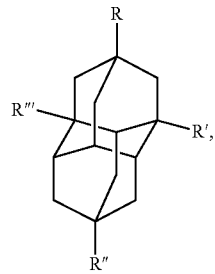
(ii)

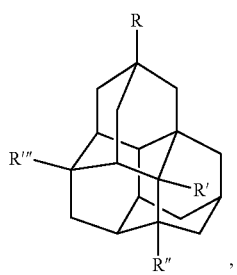
(iii)

and where R, R', R", and R'" are a hydrogen or an allyl group with at least one of R, R', R", and R'" being an allyl group.

2. The polymeric diamondoid fuel of claim 1, wherein the one or more distinct repeating units is selected from the group consisting of 3-allyltriamantane, 3,13-diallyltriamantane, 3,6,13-triallyltriamantane, and combinations thereof.

3. A polymeric diamondoid fuel, consisting of one or more distinct repeating units where each of said repeating units is a monomer having a structure selected from one of i, ii, iii, or iv:

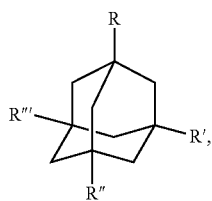
(i)

-continued

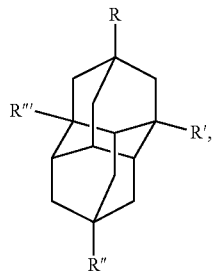
(ii)

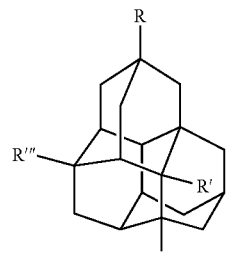
(iii)

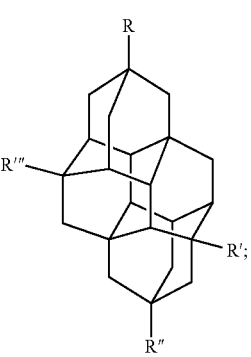
(iv)

and where R, R', R", and R'" are one of:
i) one allyl group, one cyclopropyl group, and two hydrogens;
ii) two allyl groups, one cyclopropyl group, and one hydrogen;
iii) one allyl group, two cyclopropyl group, and one hydrogen;
iv) three allyl groups and one cyclopropyl group; or
v) one allyl group and three cyclopropyl groups.

4. The polymeric diamondoid fuel of claim 3, wherein the one or more distinct repeating units is selected from the group consisting of 3,6,13-triallyl-19-cyclopropyltriamantane, 3,11,19-triallyl-6-cyclopropyltetramantane, and combinations thereof.

* * * * *